United States Patent [19]
Christensen et al.

[11] Patent Number: 6,102,879
[45] Date of Patent: Aug. 15, 2000

[54] ADJUSTABLE BACK BRACE WITH POSTERIOR WOUND CLEARANCE

[75] Inventors: Mark G. Christensen, Decatur; David P. Defrances, Atlanta, both of Ga.

[73] Assignee: Innovative Orthotics and Rehabilitation, Inc., Decatur, Ga.

[21] Appl. No.: 09/224,699

[22] Filed: Jan. 4, 1999

[51] Int. Cl.[7] ....................................................... A61F 5/00
[52] U.S. Cl. ............................................................. 602/19
[58] Field of Search ................................... 602/5, 18, 19, 602/20, 60, 61, 63; 128/869, 870; 2/455, 456, 44, 311, 312

[56] References Cited

U.S. PATENT DOCUMENTS

| | | |
|---|---|---|
| 3,351,053 | 11/1967 | Stuttle . |
| 4,640,269 | 2/1987 | Goins . |
| 4,884,562 | 12/1989 | Stone . |
| 5,086,757 | 2/1992 | Lestini . |
| 5,147,261 | 9/1992 | Smith et al. . |
| 5,178,163 | 1/1993 | Yewer, Jr. . |
| 5,207,635 | 5/1993 | Richards et al. . |
| 5,433,697 | 7/1995 | Cox . |
| 5,451,200 | 9/1995 | LaBella et al. ............................ 602/19 |
| 5,484,395 | 1/1996 | DeRoche . |
| 5,651,764 | 7/1997 | Chiu . |
| 5,690,609 | 11/1997 | Heinze, III . |
| 5,722,940 | 3/1998 | Gaylord, Jr. et al. . |

OTHER PUBLICATIONS

"Cybertech 2000, The Rigid Mechanical Advantage Orthoses," Bio Cybernetics International (1998).

*Primary Examiner*—Kim M. Lee
*Attorney, Agent, or Firm*—Jones & Askew, LLP

[57] ABSTRACT

An adjustable back brace having a posterior wound clearance. The back brace includes a pair of spaced apart support members configured to extend circumstantially about a patient's waist. Each support member has a posterior portion and an anterior portion. The anterior portions overlap one another and are adjustably secured to one another with hook and loop fasteners when the back brace is worn by the patient. A pair of inelastic straps secure and tighten the back brace about the patient's waist. Each strap is anchored approximately adjacent the patient's spine to one of the posterior portions. The straps extend toward one another across the wound clearance to rings attached to the opposite posterior portion. The straps pass through the rings to reverse direction and extend back across the wound clearance, around the patient's sides, and to the patient's anterior. By pulling the straps in opposite directions across the patient's anterior, the posterior portions are forced toward one another to narrow the wound clearance and tighten the fit of the back brace. The reverse direction operation of the straps allows the patient to more easily adjust the fit of the back brace to stabilize the spine.

21 Claims, 6 Drawing Sheets

ADJUSTABLE BACK BRACE WITH POSTERIOR WOUND CLEARANCE

FIELD OF THE INVENTION

The present invention relates to an adjustable back brace for supporting the lower back and stabilizing the spine. This invention more particularly pertains to a back brace which also provides a clearance for posterior wounds.

BACKGROUND OF THE INVENTION

Presently, there is a wide variety of back braces commercially available. These known back braces provide rigid external support to stabilize the lumbar and sacral portions of the spine. However, a majority of these braces are dedicated to only non-operative patients. Most braces do not permit access to critical areas of the spine while being worn by the patient. Often portions of the brace, or the brace as a whole, require removal so that medical treatment may be rendered to post-operative patients. Moreover, some back braces can not even be worn by post-operative patients because the braces contact the patients' wounds while being worn.

These known back braces also require assistance in order to properly fit and secure the brace to the patient. Often the patient himself does not have the dexterity or the physical strength to get in and out of a back brace. More often, the strapping systems of known back braces are too complex for the patient to utilize the brace properly. The complexity creates a problem because strapping systems are critical for stabilizing the spine.

Some other back braces are too simple in design to provide the adjustment necessary to maintain the back brace in position for stabilizing the spinal region. Over time, back braces often fail to conform to the patient's lower back and, therefore, only provide a limited degree of back support. For example, most back braces provide only for adjustments to the front of the back brace and the back is relatively unadjustable. However, if the backs of the braces are adjustable, making the adjustments is often too complex.

In response to the realized inadequacies of these earlier back braces, it became clear there is a need for an improved back brace for both non-operative and post-operative patients. This improved back brace must provide rigid spine support and adjustment to the back of the brace using non-complicated strapping systems for securing the brace to the patient. This novel back brace must also provide post-operative patients with a clearance around a back injury while the back brace is being worn.

BRIEF SUMMARY OF THE INVENTION

The present invention alleviates or solves the above-described problems in the prior art by providing an improved adjustable back brace. The present invention seeks to provide an efficient and simple strapping system for securing the back brace to the patient, while also providing clearance for treating the lower back.

Generally described, the adjustable back brace includes a pair of support members. Each support member is generally configured to extend around the sides of the patient to the patient's anterior. A posterior wound clearance is defined between posterior portions of the support members. Anterior portions of the support members are adjustable to facilitate orientation of the wound clearance with the patient's spine. While the back brace is worn, the brace avoids contact with the patient's wound and permits access to the lower back and spine by medical personnel. Inelastic straps secure the support members circumferentially about the patient's waist.

In accordance with one aspect of the present invention, one inelastic strap is anchored to each of the posterior portions of the support members, respectively. The straps extend from opposite directions across the wound clearance towards one another. Each of the straps are then slidingly coupled to the support member to which each respective strap is not anchored so that the direction of operation for each strap is reversed. Each strap then extends in opposite directions back across the wound clearance, around the patient's waist, and to the patient's anterior. By pulling the straps in opposite directions across the patient's anterior, the posterior portions of the brace are pulled toward one another to narrow the wound clearance and tighten the back brace on the user.

In accordance with another aspect of the present invention, the back brace includes an anterior thoracic support. The thoracic support includes a padded member attached to an elongated vertical member. The height of the padded member is adjustable to provide contact between the patient and the thoracic support.

The invention also provides a method of supporting the lower back and spine of a patient with the back brace described above. This method includes providing the pair of support members of the type described above. The method then includes the step of defining the wound clearance between the support members to generally correspond with the patient's lower back. The method also includes the step of adjusting the extent which anterior portions of the support members overlap one another to orient the wound clearance with the patient's spine. The invention also includes the step of extending a pair of inelastic straps from opposite directions across the wound clearance and then reversing the operational direction of the straps to extend the straps in opposite directions back across the wound clearance, around the patient's sides, and to the patient's anterior. The method also includes tensioning the support members circumferentially about the patient's waist by pulling the straps in opposite directions to force the support members toward one another and narrow the wound clearance.

Accordingly, an object of this invention is to provide an improved adjustable back brace that overcomes the aforementioned inadequacies of prior art back braces.

Another object of the present invention is to provide an improved back brace capable of providing rigid external support for the lumbar and sacral portions of a patient's spine.

Still another object of the present invention is to provide a structurally simple and economical back brace for stabilizing the patient's spine.

Yet another object of the present invention is to provide a simple back brace that requires only a waist measurement for proper sizing.

Still another object of the present invention is to provide a back brace having a broader range of adjustment when orienting the wound clearance with the spine.

The foregoing has broadly outlined some of the more significant objects and features of the present invention. These should be construed to be merely illustrative of some of the more prominent features and applications of the intended invention. Many other beneficial results can be obtained by applying the disclosed invention in a different manner or by modifying the disclosed embodiments. Accordingly, other objects and a more comprehensive understanding of the invention may be obtained by referring

BRIEF DESCRIPTION OF THE DRAWINGS

Similar reference characters refer to similar parts throughout the several views of the drawings.

DETAILED DESCRIPTION OF THE PREFERRED EMBODIMENT

With reference to the drawings, a new and improved adjustable back brace embodying the principles and concepts of the present invention and generally designated by the reference number 20 will be described.

Figure 1:
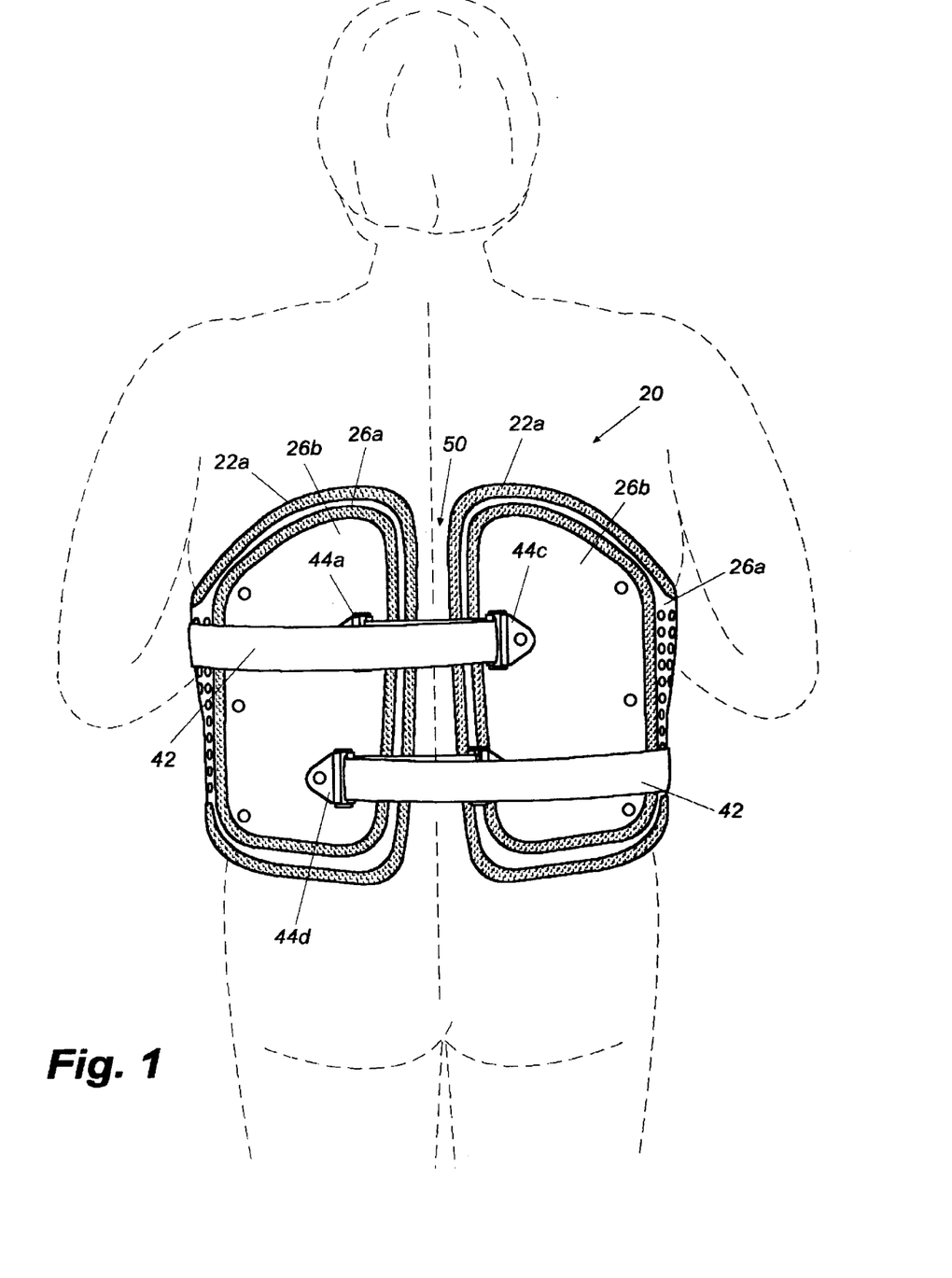
FIG. 1 illustrates a posterior view of one embodiment of an adjustable back brace worn by a patient shown in phantom and, in particular, a posterior wound clearance corresponding with the spine of the patient.
Figure 2:
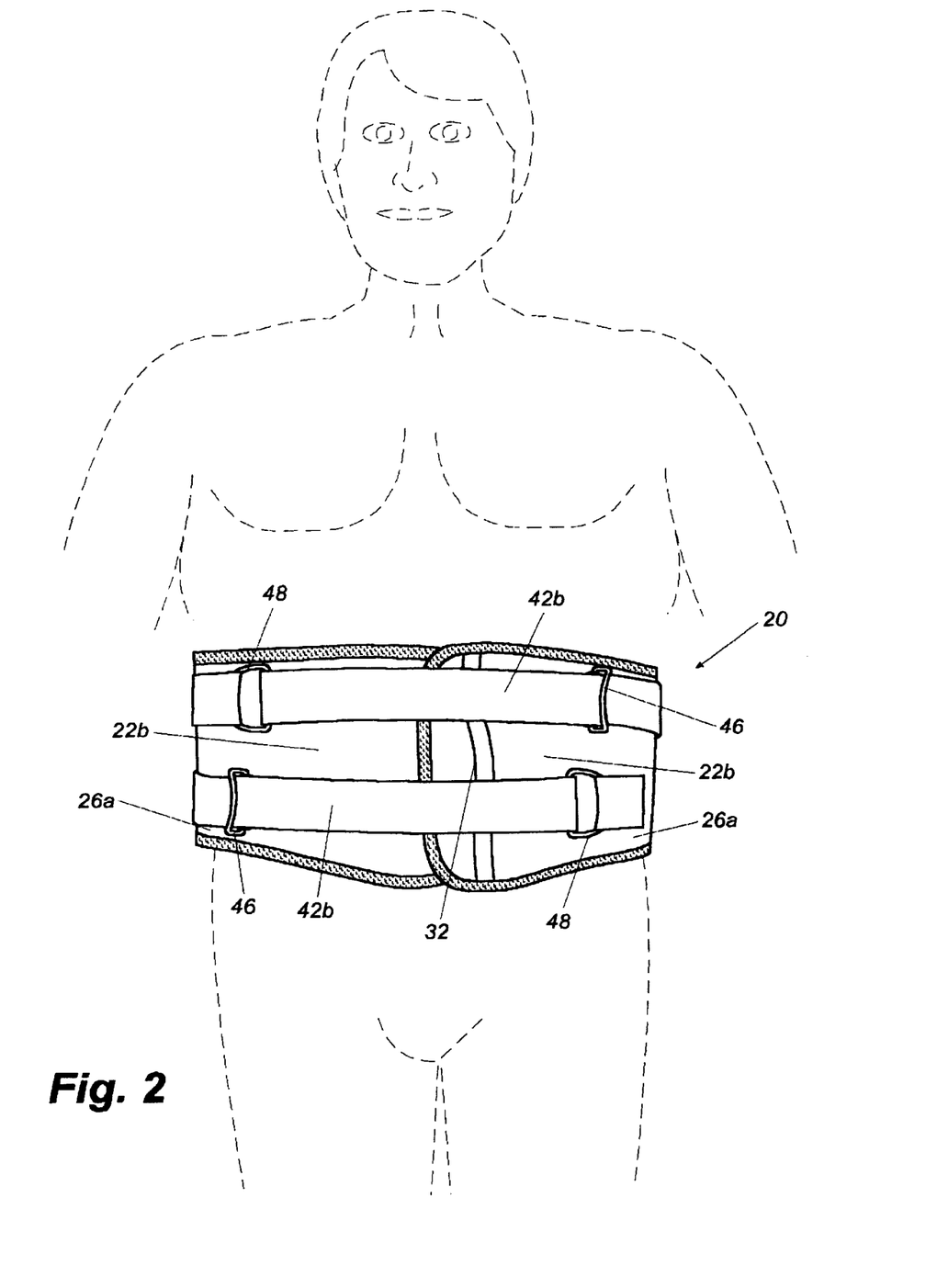
FIG. 2 illustrates an anterior view of one embodiment of the adjustable back brace shown in FIG. 1.

In accordance with one exemplary embodiment incorporating the present invention, FIG. 1 illustrates a posterior view of one embodiment of the adjustable back brace 20 worn by a patient shown in phantom. The back brace 20 extends in a symmetrical manner from a substantial vertical axis along the patient's spine, around the sides of the patient, and to the patient's anterior. FIG. 2 illustrates the anterior view of the back brace 20.

The back brace 20 includes a pair of support members 22. In the preferred embodiment, each support member 22 tapers from a larger posterior portion 22a to a smaller anterior portion 22b. The anterior portions 22b overlap at the anterior of the patient as shown in FIG. 2. The posterior portions 22a extend approximately from the patient's waist to the patient's scapula while the anterior portions 22b extend approximately from patient's waist to just below the patient's chest. A pair of separate support members is preferred over a unitary support member so that a broader range of adjustment may be obtained and to facilitate comfort.

The support members 22 include an inner foam liner 24 and overlapping exterior, rigid plastic materials 26. The liner 24 and plastic materials 26 are materials commonly utilized in the industry. For example, the plastic material may be polyethylene. Preferably, the foam liner is ¼ inch thick and the plastic material is 1/16 inch thick. The plastic material 26a is secured to the liner 24 with woven nylon ribbon 28 around the edges of the support members 22. The woven nylon ribbon also softens the edges of the back brace 20. Alternatively, the plastic material 26 may be an insert configured for being surrounded by the foam liner 24 (not shown).

Figure 3:
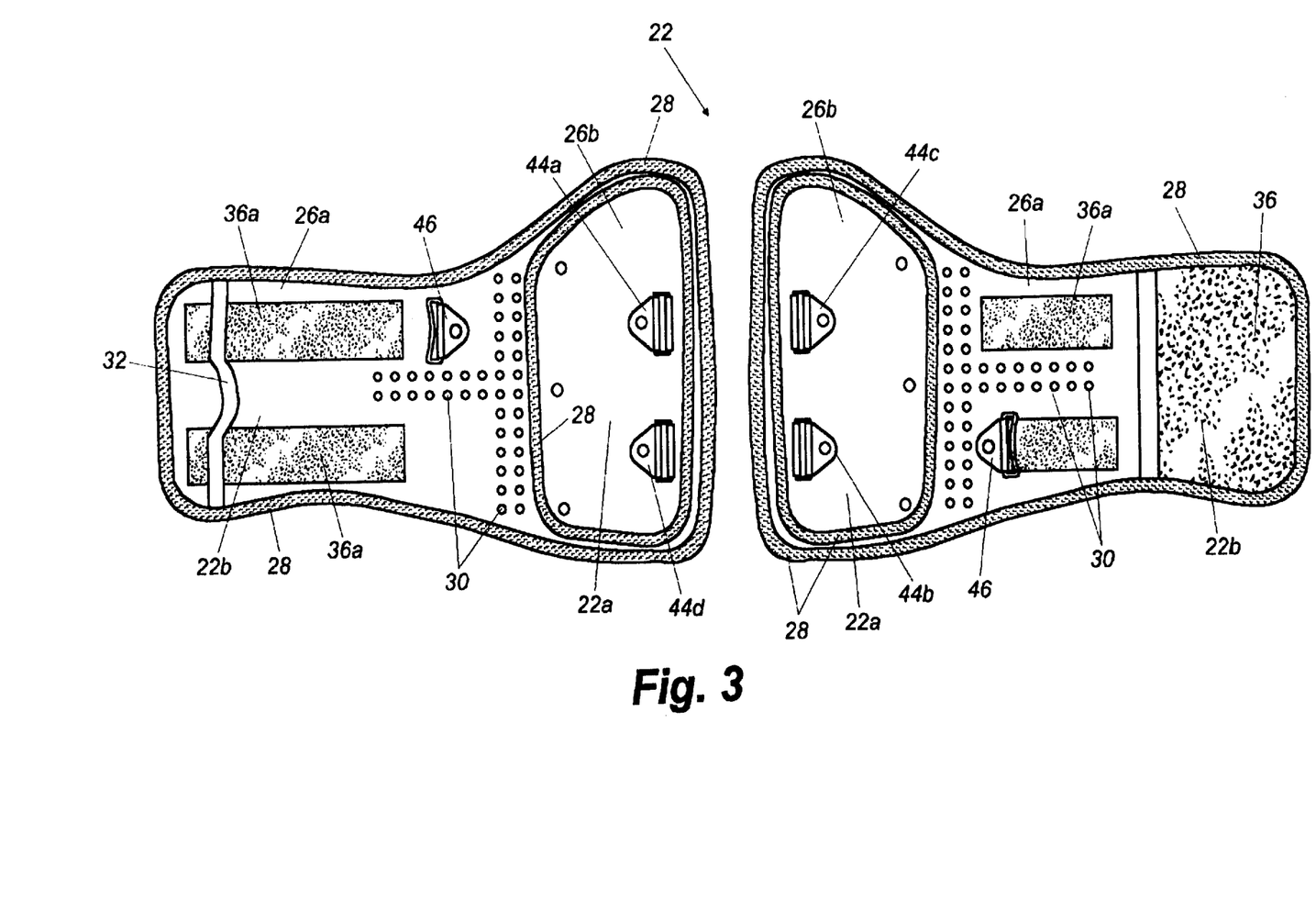
FIG. 3 illustrates one embodiment of the exterior surfaces of a pair of support members of the present invention.

FIG. 3 illustrates one embodiment of the exterior surfaces of the pair of support members. A larger plastic material 26a exteriorly extends substantially the entire length of each support member except for at least a portion of one anterior portion 22b having hook and loop fasteners as described below. A second smaller plastic material 26b on each of the posterior portions 22a overlaps the first plastic material 26a. The smaller plastic material 26b is attached to the larger plastic material 26a with nylon rivets to provide more rigid support to the patient's posterior. The combination of the plastic materials 26 at the posterior portions 22a are approximately ⅛ inch thick.

As best shown in FIG. 3, the plastic material 26 of the support members 22 also includes a plurality of air holes 30 therethrough. It is not necessary for the air holes 30 to also pass through the liner 24 because the liner generally permits air to flow through it. In other words, the liner material 24 breathes. Thus, the air holes 30 permit air from the exterior environment to pass through the back brace 20 to the patient when the brace 20 is worn. The air holes 30 are generally dispersed in the middle of each support member 22 to provide air to the patient's sides. Preferably, the air holes 30 are arranged on each support member 22 in separate arrays which extend along the height and a portion of the width of the support members 22 as best shown in FIG. 3.

Figure 4:
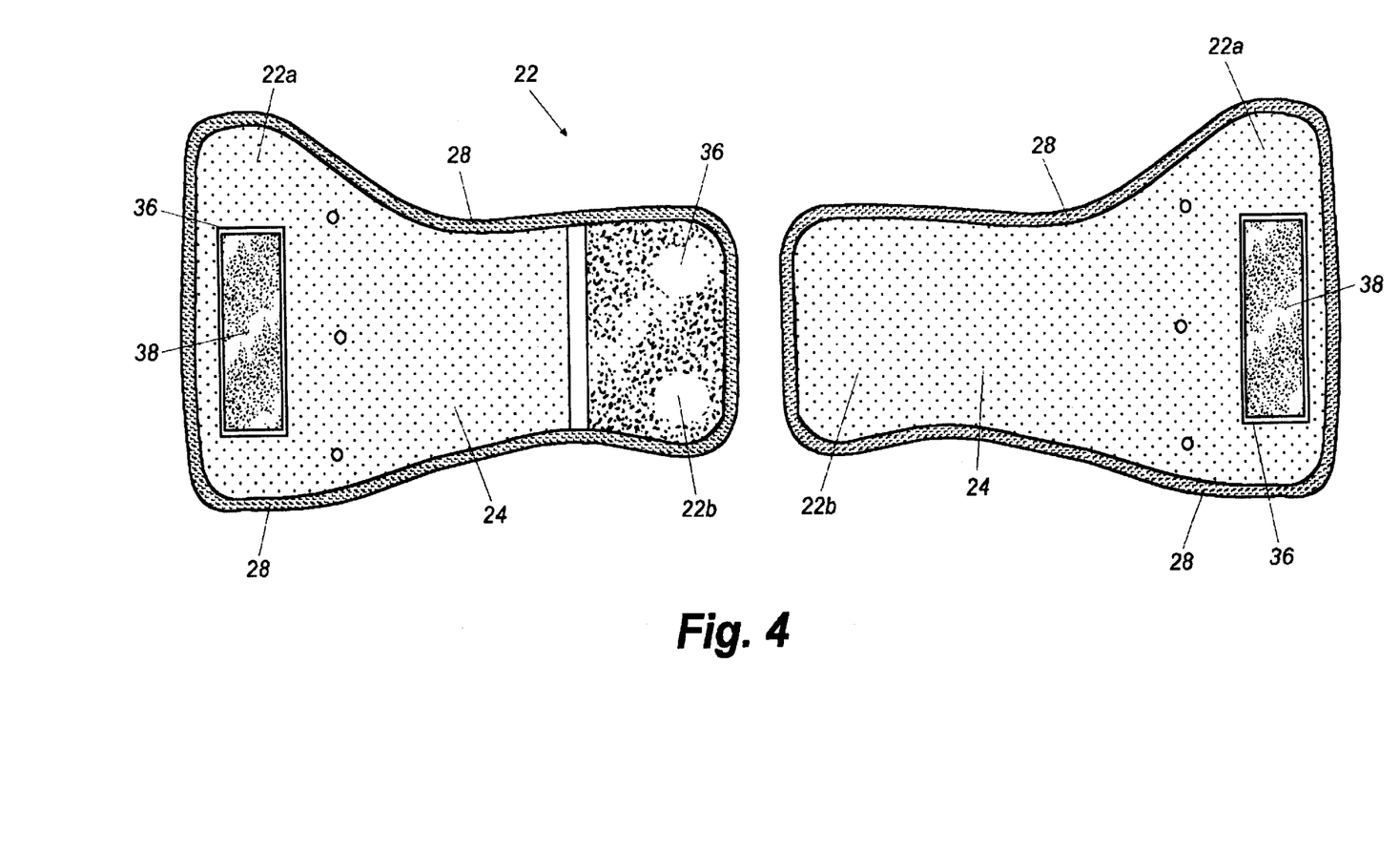
FIG. 4 illustrates one embodiment of the interior surfaces of the pair of support members shown in FIG. 3.

To get in and out of the back brace 20, the support members are adjustably secured to one another with hook and loop fasteners 36 at the patient's anterior. FIG. 2 best illustrates the anterior portions 22b of the support members 22 overlapping and FIG. 4 illustrates the interior surfaces of the support members 22. The inside surface of the patient's left support member 22 includes the hook portion of the hook and loop fasteners 36. The exterior surface of the patient's right support member 22 includes the loop portion of the hook and loop fasteners 36 as shown in FIG. 3. FIGS. 2 and 3 also illustrate a substantially vertically oriented grip-strap 32. The ends of the grip-strap are stitched to the exterior anterior portion of one of the support members. The grip-strap 32 forms a loop which the patient can grasp to facilitate securing of said back brace about the patient's waist.

In FIG. 4, hook and loop fasteners 36 are also utilized to detachably secure adjustable lordosis pads 38 to the interior surface of the posterior portions 22a of the support members 22. The lordosis pads are made of dense foam of various sizes and may be variably positioned on the interior of the support members 22 as a result of the hook and loop fasteners. The lordosis pads are removed periodically for cleaning. Alternatively, the lardosis pads may be carved to meet any degree of lordosis.

As shown in FIG. 3, the support members 22 each have various rings attached to their exterior. The rings are for receiving inelastic straps 42 used for securing and tensioning the support members circumferentially about the patient's waist. Preferably, the straps 42 are woven nylon. The rings are attached to the exterior of the brace 20 with nylon rivets. The posterior portion 22a of each support member 22 includes a pair of vertically aligned metal oval rings 44 with plastic roller sleeves. The roller sleeves allow the straps to slidingly engage the support members. Each support member further includes a nylon retaining ring 46 positioned approximately midway on the exterior of each support member 22.

Figure 5:
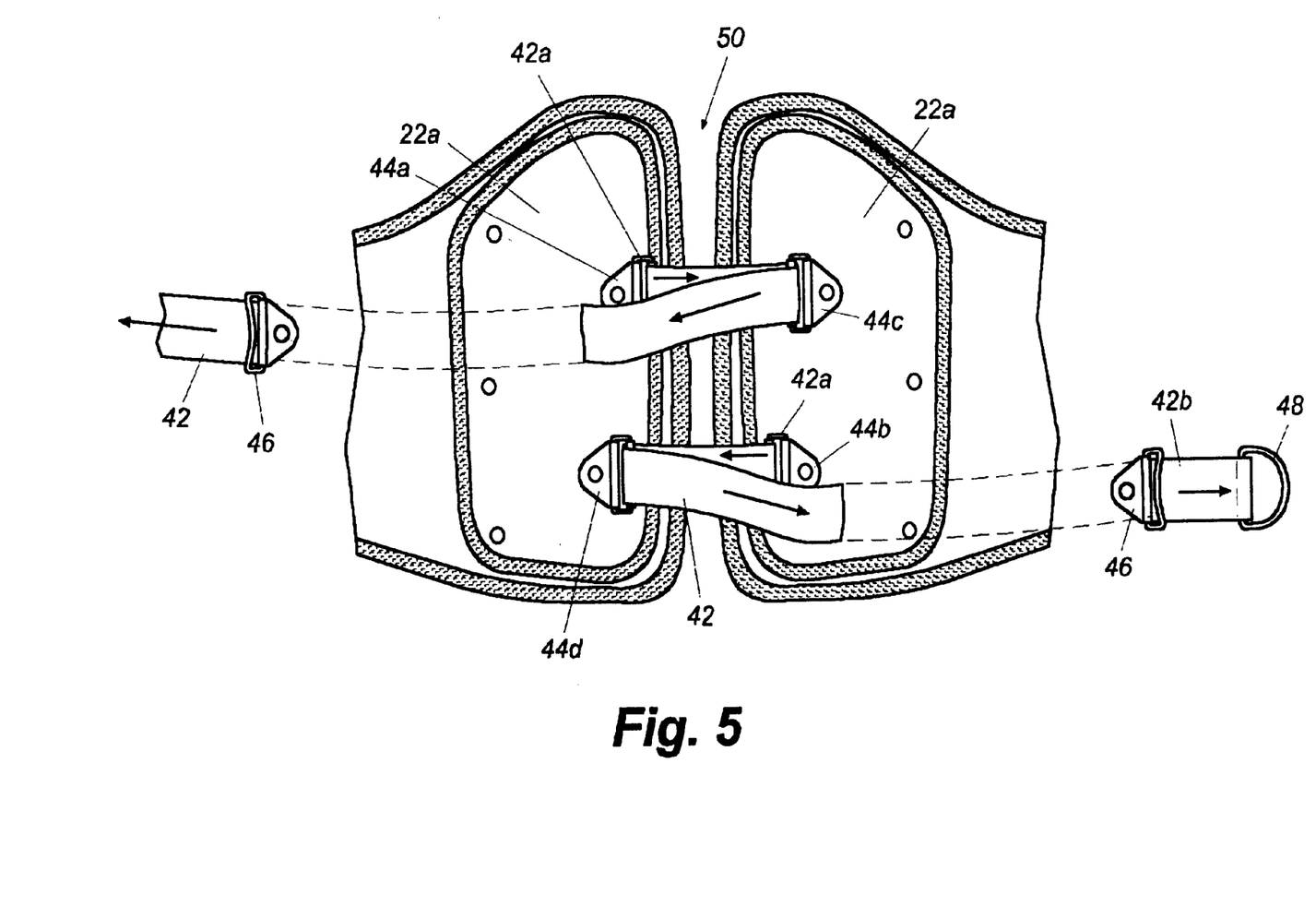
FIG. 5 is a partial view of one embodiment of the back brace of the present invention illustrating, in particular, the reverse direction operation of inelastic straps across the wound clearance.

The arrangement of the inelastic straps 42 is shown in detail in FIG. 5. FIG. 5 is a exterior view of the posterior portions 22a of the back brace 20. A fixed end 42a of one strap 42 is anchored to the upper ring 44a on the left posterior portion 22a and a fixed end 42a of a second strap 42 is anchored to the lower ring 44b on the right posterior portion 22a. As best shown in FIG. 1, the straps 42 are anchored adjacent the patient's spine. Each strap 42 then proceeds across a wound clearance 50 to the other support member and passes through the ring 44 which is horizontally aligned with the anchoring ring 44 to which it is attached. For example, the strap 42 anchored with ring 44a passes through ring 44c and the strap 42 anchored with ring 44b passes through ring 44d.

Because of the rings' roller sleeves, the straps 42 slidingly engage the support member 22 and are able to reverse direction. After reversing direction, each strap 42 overlaps itself and its anchoring support member 22. The straps 42 cross back over the wound clearance 50 overlapping themselves in substantially a horizontal plane so that obstruction of the wound clearance 50 is minimized. The straps 42 continue to extend in opposite directions around the patient's waist, through respective rings 46, and to the patient's anterior so that free ends 42b of the straps 42 are easily accessible by the patient. The upper strap 42 extends around the patient's left and the lower strap 42 extends around the patient's right. The free ends 42b are fitted with plastic oval thumb rings 48 to permit the patient to obtain an easy grip. The free ends 42b may also be secured to the exterior of the back brace 20 with hook and loop fasteners 36a. The one portion of the hook and loop fasteners 36a for securing the free ends 42b is shown in FIG. 3. The other portion is on the inner side (not shown) of the free ends 42b.

Defined between the posterior portions 22a of the support members 22 is the wound clearance 50. The straps extend back and forth across the wound clearance 50 as best shown in FIGS. 1 and 5. The wound clearance 50 generally corresponds with the patient's lower back and can be narrowed by pulling the free ends 42b of the straps 42 in opposite directions. The straps 42 force the support members 22 towards one another to narrow the wound clearance 50 and tighten the fit of the back brace 20. Preferably, the width of the wound clearance is narrowed to approximately 1 to 2 inches. The posterior portions of the support members may occasionally be forced toward one another to such an extent that the wound clearance is closed. However, the extent which the anterior portions overlap can be modified to adjust the width of the wound clearance to a desired dimension when the brace is tightened.

Figure 6:
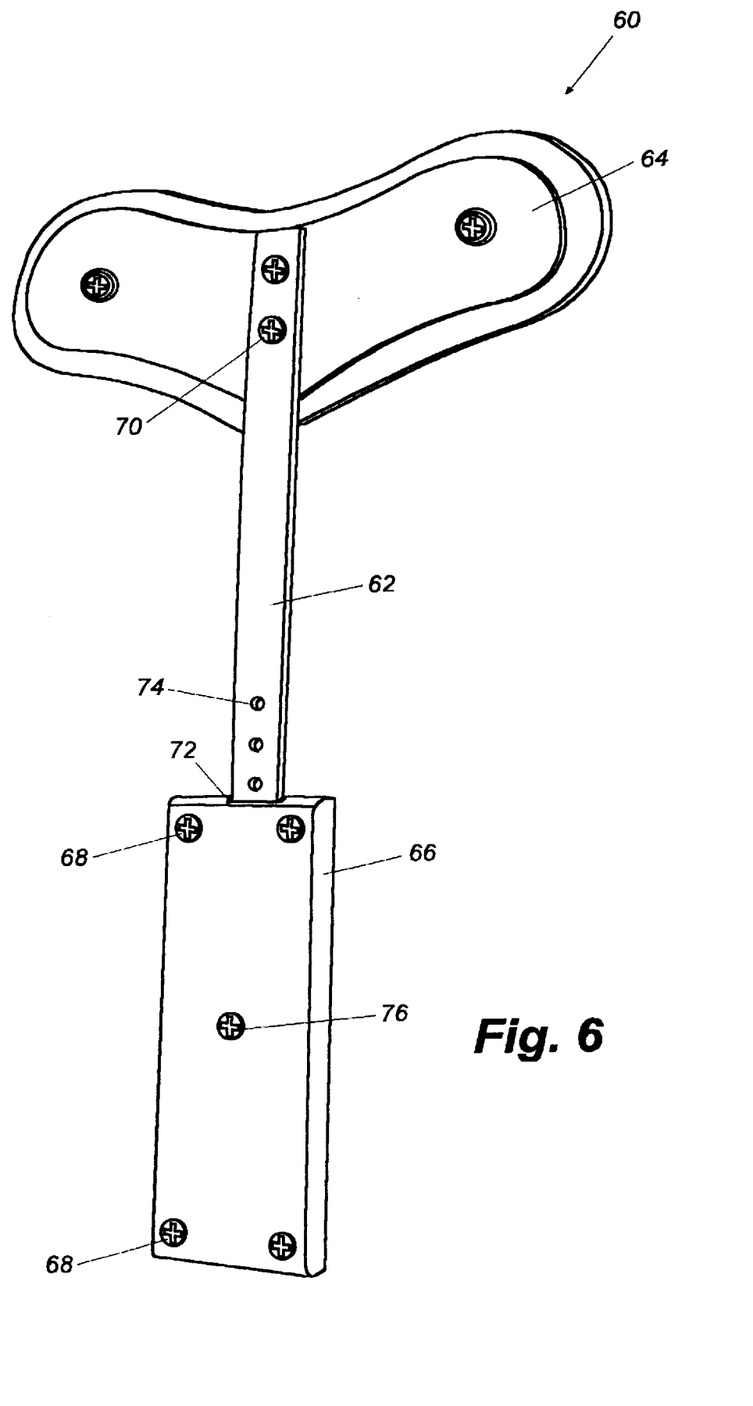
FIG. 6 illustrates one embodiment of an anterior thoracic support for use with the adjustable back brace of the present invention.

Because the anterior portions of the support members overlap as described above, the brace 20 permits the wound clearance to more accurately correspond with the patient's spine. Simply, the wound clearance 50 may be precisely oriented with the spine and the preferred wound clearance maintained by adjusting the overlapping portions of the support members 22. A single-membered brace can not provide as broad a range of adjustment and account for the varying sizes of patients as does the present invention FIG. 6 illustrates one embodiment of an anterior thoracic support 60. The thoracic support 60 includes an elongated vertical member 62, a padded member 64, and an attachment block 66. The block 66 detachably secures the vertical member 62 to the anterior of the back brace 20 with fasteners 68 which are inserted through matching holes (not shown) in the back brace 20. The padded member 64 is attached to the vertical member 62 with fasteners 70. The padded member 64 provides contact between the patient and the thoracic support 60. The attachment block 66 has a substantially vertically oriented opening 72 extending therethrough for receiving the vertical member 62. The vertical member 62 slidingly engages the block 66 to provide a vertical height adjustment for the padded member 64 relative to the support members 22. The vertical member 62 includes several evenly-spaced holes 74 to allow for height adjustments. The height of the padded member is retained by a height adjustment screw 76 which is sized to be received by the evenly-spaced holes 74.

The use of the back brace 20 as described above constitutes an inventive method of the present invention in addition to the back brace 20 itself. In practicing the method of supporting the lower back and spine of a patient with the back brace 20 as described above, the steps include providing a pair of support members 22 of the type described above. The method then includes the step of defining a wound clearance 50 between the support members 22 to generally correspond with the patient's lower back as described above. The method also includes the step of adjusting the extent which anterior portions 22b of each support member overlaps one another to precisely orient the wound clearance with the patient's spine. The invention also includes the step of extending a pair of inelastic straps 42 from opposite directions across the wound clearance and then reversing the operational direction of the straps to extend the straps in opposite directions back across the wound clearance, around the patient's sides, and to the patient's anterior. The method also includes tensioning the support members circumferentially about the patient's waist by pulling the straps in opposite directions to force the support members toward one another and narrow the wound clearance.

The present invention has been illustrated in great detail by the above specific examples. It is to be understood that these examples are illustrative embodiments and that this invention is not to be limited by any of the examples or details in the description. Those skilled in the art will recognize that the present invention is capable of many modifications and variations without departing from the scope of the invention. Accordingly, the detailed description and examples are meant to be illustrative and are not meant to limit in any manner the scope of the invention as set forth in the following claims. Rather, the claims appended hereto are to be construed broadly within the scope and spirit of the invention.

What is claimed is:

1. An adjustable back brace for supporting the spine of a patient, comprising:

a pair of support members configured to extend in a symmetrical manner from a substantially vertical axis along the spine to the patient's anterior;

a posterior wound clearance defined between said support members and corresponding with the patient's spine; and no more than two inelastic straps for securing and tensioning said support members circumferentially about the patient's waist, each of said straps having a fixed and free end, said fixed end of each said strap anchored adjacent the spine to one of said support members, said strap extending from said one support member across said wound clearance to the other of said support members, said strap slidingly coupled to said other support member and reversing direction such that said strap passes back across said wound clearance and said free end of said strap extends around the patient's waist to the patient's anterior, said straps capable of forcing said support members toward one another to narrow said wound clearance and tighten the fit of said back brace when said free ends of said straps are pulled in opposite directions;

wherein each said strap is attachable to at least one of said support members at the patient's anterior, thereby maintaining said support members in a tightened position; and wherein each said strap passes back across said wound clearance such that each said strap overlaps itself in substantially a horizontal plane so that obstruction of said wound clearance is minimized.

2. The adjustable back brace of claim 1 wherein said support members overlap one another at the patient's anterior and are adjustably secured to one another.

3. The adjustable back brace of claim 1 wherein each said support member tapers from a larger posterior portion to a smaller anterior portion such that said anterior portions are sized to extend approximately from the patient's waist to just below the patient's chest and said posterior portions are sized to extend approximately from the patient's waist to the patient's scapula.

4. The adjustable back brace of claim 1 further comprising a substantially vertically oriented grip-strap having ends coupled to one of said support members to facilitate securing of said back brace about the patient's waist.

5. The adjustable back brace of claim 1 further comprising an anterior thoracic support, said thoracic support comprising an elongated vertical member, an attachment means for detachably securing said vertical member to said back brace, and a padded member coupled to said vertical member for providing contact between the patient and said thoracic support, said vertical member slidingly engaged to said attachment means to provide a vertical height adjustment for said padded member relative to said support members.

6. The adjustable back brace of claim 5 wherein said attachment means is a block having a substantially vertically oriented opening extending therethrough for receiving said vertical member therein.

7. The adjustable back brace of claim 1 wherein said support members comprise an exterior plastic material coupled to an inner foam liner.

8. The adjustable back brace of claim 7 wherein said plastic material comprises a plurality of air holes therethrough to permit passage of air through said back brace.

9. The adjustable back brace of claim 1, wherein said strap is slidingly coupled to said other support member by passing through a metal ring fixed to said other support member, said metal ring holding a roller sleeve, the roller sleeve operative to turn on the metal ring, thereby permitting said strap to freely slide through the metal ring.

10. An adjustable back brace for supporting the lower back and spine of a patient, comprising:

a pair of support members configured to extend from approximately the patient's spine, around the sides of the patient, and overlap at the anterior of the patient, said support members tapering from the posterior to the anterior of the patient to define larger posterior portions and smaller anterior portions;

a wound clearance defined between said posterior portions and generally corresponding with the patient's lower back, and said anterior portions operable to overlap one another to an adjustable extent at the patient's anterior to orient said wound clearance with the patient's spine; and no more than two inelastic straps for securing and tensioning said support members circumferentially about the patient's waist, each of said straps having a fixed and free end, said fixed end of each said strap anchored adjacent the spine to one of said support members, said strap extending from said one support member across said wound clearance to the other of said support members, each said strap slidingly coupled to said other support member and reversing direction such that said strap passes back across said wound clearance and said free end of said strap extends around the patient's waist to the patient's anterior, said straps capable of forcing said support members toward one another to narrow said wound clearance and tighten the fit of said back brace when said free ends of said straps are pulled in opposite directions;

wherein each said strap passes back across said wound clearance such that each said strap overlaps itself in substantially a horizontal plane so that obstruction of said wound clearance is minimized.

11. The adjustable back brace of claim 10 wherein said anterior portions are adjustably secured to one another.

12. The adjustable back brace of claim 10 wherein said anterior portions are sized to extend approximately from the patient's waist to just below the patient's chest and said posterior portions are sized to extend approximately from the patient's waist to the patient's scapula.

13. The adjustable back brace of claim 10 further comprising an anterior thoracic support, said thoracic support comprising an elongated vertical member, an attachment means for detachably securing said vertical member to said back brace, and a padded member coupled to said vertical member for providing contact between the patient and said thoracic support, said vertical member slidingly engaged to said attachment means to provide a vertical height adjustment for said padded member relative to said support members.

14. The adjustable back brace of claim 13 wherein said attachment means is a block having a substantially vertically oriented opening extending therethrough for receiving said vertical member therein.

15. The adjustable back brace of claim 10 wherein said support members comprise an exterior plastic material coupled to an inner foam liner.

16. The adjustable back brace of claim 15 wherein said plastic material comprises a plurality of air holes therethrough to permit the passage of air through said back brace.

17. The adjustable back brace of claim 10, wherein said strap is slidingly coupled to said other support member by passing through a metal ring fixed to said other support member, said metal ring holding a roller sleeve, the roller sleeve operative to turn on the metal ring, thereby permitting said strap to freely slide through the metal ring.

18. An adjustable back brace for supporting the lower back and spine of a patient, comprising:

a pair of support members configured to extend from approximately the patient's spine, around the sides of the patient, and overlap one another at the anterior of the patient, said support members tapering from the posterior to the anterior of the patient to define larger posterior portions and smaller anterior portions, and each said support member comprising a plurality of air holes therethrough to permit the passage of air through said back brace;

a wound clearance defined between said posterior portions and generally corresponding with the patient's lower back, and said anterior portions operable to overlap one another at the patient's anterior to precisely orient said wound clearance with the patient's spine;

a substantially vertically oriented grip-strap having ends coupled to one of said support members to facilitate securing of said back brace about the patient's waist; and no more than two inelastic straps for securing and tensioning said support members about the patient's waist, each said strap having a fixed end anchored adjacent the spine to one of said posterior portions, said straps extending from said anchoring posterior portion across said wound clearance to the other of said support members, each said strap then passing through a ring coupled to said other posterior portion to permit said straps to reverse direction such that each said strap extends back across said wound clearance and around the patient's side to the patient's anterior, said straps capable of forcing said posterior portions toward one another to narrow said wound clearance and tighten the fit of said back brace when said straps are pulled in opposite directions.

19. The adjustable back brace of claim 18 further comprising an anterior thoracic support, said thoracic support comprising an elongated vertical member, a block for detachably securing said vertical member to said back brace, and a padded member coupled to said vertical member for providing contact between the patient and said thoracic support, said block having a substantially vertically oriented opening therethrough for receiving said vertical member therein, and said vertical member slidingly engaged to said block in said vertically oriented opening to provide a vertical height adjustment for said padded member.

20. The adjustable back brace of claim 18, wherein said ring has a roller sleeve, the roller sleeve operative to turn on the ring, thereby permitting each said strap to freely slide through the ring.

21. A method of supporting the lower back and spine of a patient with a back brace, comprising the steps of:

providing a pair of support members configured to extend in a symmetrical manner from a substantially vertical axis along the spine of the patient;

defining a wound clearance between said support members to generally correspond with the patient's lower back;

adjusting the extent which an anterior portion of each said support member overlaps one another to precisely orient said wound clearance with the patient's spine extending no more than two inelastic straps from opposite directions across said wound clearance and then reversing the operational direction of said straps to extend said straps in opposite directions back across said wound clearance, around the patient's sides, and to the patient's anterior; and tensioning said support members circumferentially about the patient's waist by pulling said straps in opposite directions to force said support members toward one another and narrow said wound clearance.

* * * * *